United States Patent [19]

Mahony, III

[11] Patent Number: 5,062,843
[45] Date of Patent: Nov. 5, 1991

[54] INTERFERENCE FIXATION SCREW WITH INTEGRAL INSTRUMENTATION

[76] Inventor: Thomas H. Mahony, III, 1730 Wood Ave., Colorado Springs, Colo. 80903

[21] Appl. No.: 476,252

[22] Filed: Feb. 7, 1990

[51] Int. Cl.⁵ ............................................. A61F 2/08
[52] U.S. Cl. ....................................... 606/53; 606/65; 606/76; 606/77
[58] Field of Search .................................... 606/60–62, 606/65, 72–73, 76–77, 86, 104; 623/13, 16

[56] References Cited

U.S. PATENT DOCUMENTS

| | | |
|---|---|---|
| D. 245,516 | 8/1977 | Treace . |
| 2,570,465 | 10/1951 | Lundholm .............................. 606/73 |
| 4,539,981 | 9/1985 | Tunc ...................................... 606/72 |
| 4,590,928 | 5/1986 | Hunt et al. . |
| 4,716,893 | 1/1988 | Fischer et al. ......................... 606/65 |
| 4,834,752 | 5/1989 | Van Kampen ......................... 606/77 |
| 4,870,957 | 10/1989 | Goble et al. . |
| 4,898,186 | 2/1990 | Ikada et al. ............................. 606/62 |
| 4,927,421 | 5/1990 | Goble et al. . |

FOREIGN PATENT DOCUMENTS

| | | |
|---|---|---|
| 0260970 | 3/1988 | European Pat. Off. . |
| 3630863 | 3/1988 | Fed. Rep. of Germany . |
| 2622790 | 5/1989 | France . |
| 137525 | 2/1988 | U.S.S.R. ................................ 606/73 |

OTHER PUBLICATIONS

Brochure, "M. Kurosaka Interference Fixation Screw System".

*Primary Examiner*—Robert A. Hafer
*Assistant Examiner*—Kerry Owens
*Attorney, Agent, or Firm*—Ice Miller Donadio & Ryan

[57] ABSTRACT

A fixation screw for securing a bone graft of a tendon section in place in a ligament tunnel is formed from a biocompatible plastic or bioabsorbable material. The tendon section is used to replace a ligament and has a tendon section attached at each end to bone grafts. The fixation screw is tightened between the bone graft and bone surrounding the ligament tunnel to secure the bone graft in place by forcing it against the bone surrounding the ligament tunnel. The material is soft compared to bone so that threads of the fixation screw do not cut into the bone graft or bone graft or bone surrounding the ligament tunnel when the fixation screw is tightened. The fixation screw is formed to have integral instrumentation. A body is molded or fabricated as one piece from the material and has a threaded end, formed as an interference screw, and relatively thicker handle portion connected to each other. The handle portion forms the integral instrument in that it is grasped to turn the fixation screw to tighten it. The threaded end is inserted between the bone graft and bone surrounding the ligament tunnel. The handle is turned to tighten the threaded end between the bone graft and surrounding bone. After the fixation screw has been tightened, the portion of the fixation screw which extends beyond the surface of the bone at which the ligament tunnel opens is trimmed off, leaving all surfaces flush.

10 Claims, 1 Drawing Sheet

INTERFERENCE FIXATION SCREW WITH INTEGRAL INSTRUMENTATION

BACKGROUND AND SUMMARY OF THE INVENTION

This invention relates to fixation screws, and more particularly to fixation screws which are used to secure bone/ligament or tendon grafts in place in boney tunnels throughout the body.

Ligaments are connective tissue which join surfaces of bones together in a joint. They act to limit the motion of the bones of the joint relative to each other. Injuries to ligaments are not uncommon, particularly in patients who are active in sports. The anterior cruciate ligament of the human knee is especially susceptible to damage. Unfortunately, when an anterior cruciate ligament is damaged, it must often be replaced because it frequently never heals.

One method of replacing damaged ligaments is to use a section of tendon grafted from the knee cap or patella. A portion of tendon is excised from the patella. A portion of the bone (bone graft) to which each end of the tendon section is attached is excised with the tendon section. A hole or boney tunnel (ligament tunnel) is drilled through the femur and tibia. The tendon graft is inserted into the ligament tunnel in the femur and the ligament tunnel in the tibia and positioned so that it is centered in the two ligament tunnels. That is, an equal length of tendon graft is disposed in both the femur and in the tibia. A fixation screw is then tightened in the ligament tunnel between the bone graft and the side of the ligament tunnel in the bone to affix the bone graft in place. The tendon section is now appropriately tensioned and the bone graft attached to the other end of the tendon section is secured with a screw.

Heretofore, metal fixation screws have been used to affix the bone grafts in place. Such screws may be designed to be interference screws or may be standard bone screws with blunt threads. The interference screw is designed so that the screw will not cut into the bone graft or the side of the boney tunnel. Rather, when the interference screw is tightened in place, it forces the bone graft tightly against the side of the boney tunnel so that the bone graft is held in place by friction.

Metal screws do not always act as interference screws, even if designed as such. The threads of the metal screws can cut into the bone grafts and damage or even destroy the bone grafts. Further, if either the screw or the bone graft is slightly oversize, or the boney tunnel in which the bone graft is to be secured is slightly undersized, the lack of resiliency on the part of the threads of the metal screw can cause too much force to be exerted on the bone graft as the metal screw is tightened. This too can damage or destroy the bone graft. If this happens, the surgeon may be left without a bone graft to use to secure an end of the tendon graft in place. The tendon graft may then be useless. If this happens, either a new tendon graft must be taken from the patella or, if there is not sufficient tendon left in the patella to take a new graft, a different technique for replacing the damaged ligaments must be used such as an artificial ligament prosthesis. In most cases, however, using a natural part of the patient's body to replace the damaged ligament is preferable. Artificial ligaments have biocompatibility and biodegradation problems which a tendon section from the patient's own patella does not have.

Another problem with the metal screws is that the length of tendon which can be grafted varies between individual patients. So too do the lengths of the ligament tunnels drilled in the tibia and femur. Consequently, when the tendon grafts are properly positioned in the ligament tunnels drilled in the femurs and tibias of patients, the distances the bone grafts are recessed in the ligament tunnels in the femurs and tibias vary from patient to patient. The screw which is used to affix the bone graft in place must be long enough to have adequate purchase against the bone graft but short enough so that any portion extending beyond the surface of the tibia or femur when the screw is tightened is minimized and preferably eliminated. Therefore, the surgeon must have available screws in several different lengths to be able to select ones having the proper length.

Finally, metal screws require separate instrumentation. In this context, "instrumentation" means a device which is used to facilitate the installation of the screw. Here, such instrumentation is some type of fastening device, such as a hex driver, which is used to tighten the screws. This requires that sterile instrumentation (fastening device) be available to the surgeon. This increases the number of sterile items that must be maintained in the operating room.

It is an object of this invention to provide a fixation screw for securing in place in a ligament tunnel bone grafts of a tendon graft used to replace ligaments. The fixation screw is formed as an interference screw from a relatively soft material to prevent the threads of the screw from cutting into and damaging the bone grafts.

It is another object of this invention to provide a fixation screw where any excess projecting beyond the surface of the bone at which the ligament tunnel opens can be trimmed off after the fixation screw has been tightened.

It is yet another object of this invention to provide a fixation screw which has integral instrumentation used to tighten the screw in place and which is cut off when the excess screw material is trimmed after the screw has been tightened.

Additional features and advantages of the invention will become apparent to those skilled in the art upon consideration of the following detailed description of a preferred embodiment, exemplifying the best mode of carrying out the invention as presently perceived. The detailed description particularly refers to the accompanying figures in which.

Figure 1:
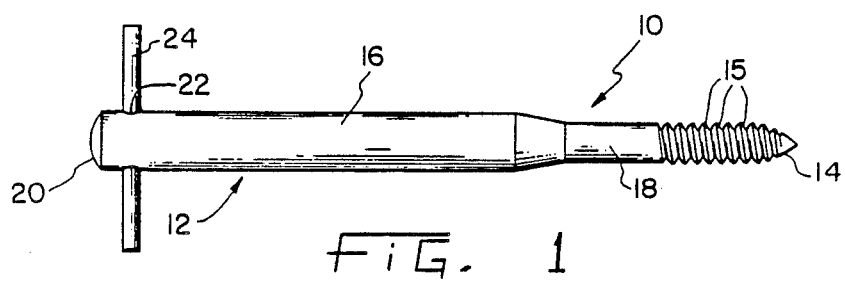
FIG. 1 is a perspective view of a fixation screw formed in accordance with this invention.

Referring to FIG. 1, a fixation screw 10 formed in accordance with this invention has a body 12 with a threaded end 14. Threaded end 14 has threads 15. Threaded end 14 is formed as an interference screw. Body 12 has a relatively thicker handle portion 16 connected to threaded end 14 by a necked down portion 18. At an end 20 opposite threaded end 14, handle portion 16 has a hole 22 extending transversely therethrough. A rod 24 can be inserted through hole 22 to facilitate tightening of fixation screw 10.

Body 12 of fixation screw 10 is fabricated as a single piece from a material which is relatively soft compared to bone. That is, the material from which body 12 is molded is sufficiently soft so that threads 15 of threaded end 14 of body 12 will yield when compressed against bone rather than cutting into the bone. Such material could be a bioabsorbable or biocompatible material. Illustratively, body 12 is machined from ultra-high molecular weight polyethylene which is a biocompatible plastic. Body 12 could also be molded such as from a biocompatible plastic.

By fabricating body 12 of fixation screw 10 from a relatively soft material, the threads 15 of threaded end 14 will not cut into the bone grafts when fixation screw 10 is tightened in place. Threads 15 will yield when compressed between the bone grafts and bone, as discussed in more detail below, rather than cutting into them.

Handle portion 16 comprises instrumentation which is used to tighten fixation screw 10. That is, when fixation screw 10 is being installed, handle portion 16 is grasped by the surgeon and turned to tighten threaded end 14 as will be described in more detail below. By fabricating body 12 as a single piece, threaded end 14, handle portion 16, and necked down portion 18 are formed as an integral unit. Thus, fixation screw 10 includes integral instrumentation in that handle portion 16 and threaded end 14 are fabricated as integral pieces of body 12. Although rod 24 is shown as a separate piece in FIG. 1, it should be understood that it could be fabricated as part of fixation screw 10. For example, rod 24 and body 12 could be molded as a single piece.

Figure 2:
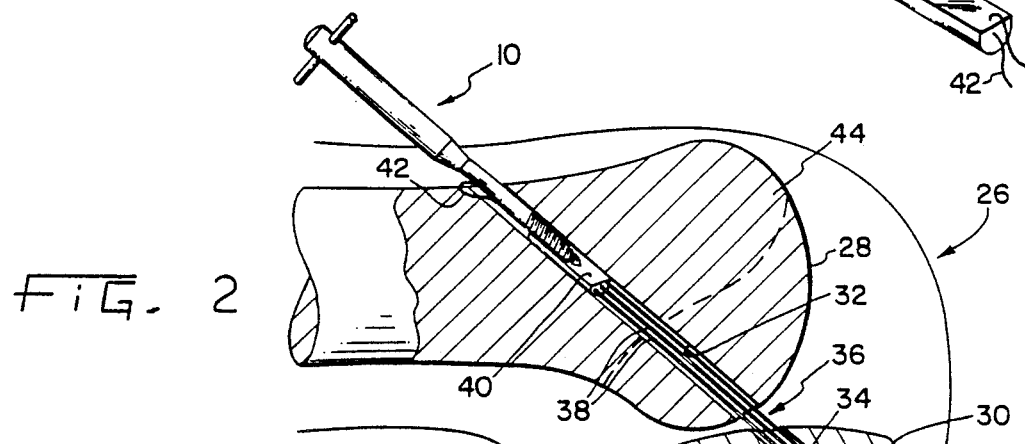
FIG. 2 is a perspective view of a knee joint in which a tendon graft used to replace the cruciate ligament of the knee has a bone graft at one end secured in place to the cruciate bone surrounding that end by the fixation screw of this invention.

Referring to FIG. 2, a knee joint 26 has a femur 28 and a tibia 30. Ligament tunnels 32, 34, are drilled through femur 28 and tibia 30, respectively, so that they are coaxial when the knee joint 26 is in flexion, as shown in FIG. 2. A tendon graft 36 is inserted in ligament tunnels 32, 34 and secured in place as described below to replace the cruciate ligament (not shown) of knee joint 26.

Figure 3:
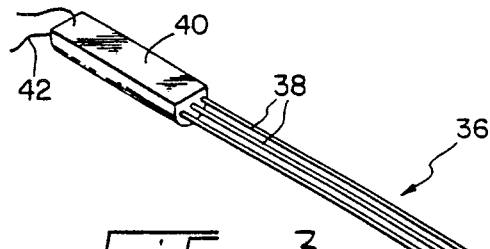
FIG. 3 is a perspective view of the tendon graft of FIG. 2.

Tendon graft 36 is taken from the patella (not shown) of knee joint 26. As best shown in FIG. 3, tendon graft 36 comprises a section of tendon 38 attached at each end to bone grafts 40. When taking tendon graft 36 from the patella, bone grafts 40, to which the ends of tendon section 38 are attached, are excised from the patella. Illustratively, bone grafts 40 are semi-cylindrical sections of bone sized to fit within ligament tunnels 32, 34. Typically, ligament tunnels 32, 34 would either be seven millimeters or ten millimeters in diameter. Similarly, the diameters or thicknesses of bone grafts 40 would be about seven or ten millimeters, respectively.

After tendon graft 36 is taken from the patella, it is inserted into ligament tunnels 32, 34. Before this is done, sutures 42 are usually placed in bone grafts 40 to hold bone grafts 40 in ligament tunnels 32, 34 while fixation screws 10 are put in place. Tendon graft 36 is positioned in ligament tunnels 32, 34, so that approximately an equal amount of tendon section 38 is in ligament tunnel 32 in femur 28 and in ligament tunnel 34 in tibia 30.

Figure 4:
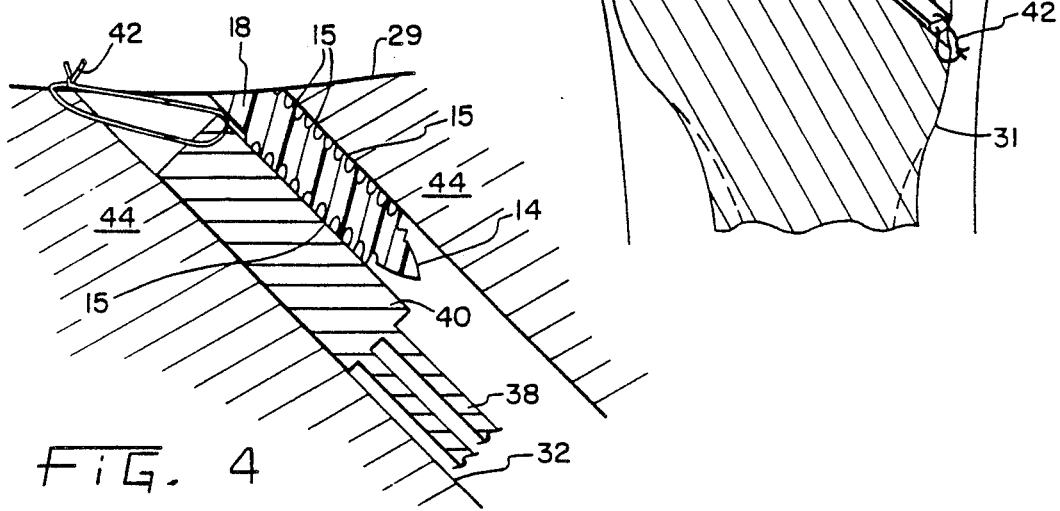
FIG. 4 is an exploded perspective view of FIG. 2 showing the bone graft in the ligament tunnel in the femur held in place by the fixation screw of this invention.

As mentioned above, the length of tendon graft 36 varies from patient to patient. Also, the size of the femur and tibia, and thus the lengths of femur and tibia tunnels 32, 34, also varies from patient to patient. Consequently, when tendon graft 36 is properly positioned in ligament tunnels 32, 34, the bone grafts 40 will be recessed from the opening of ligament tunnel 32 at anterior surface 29 of femur 28 and from the opening of ligament tunnel 34 at an anterior surface 31 of tibia 30 distances which vary from patient to patient After tendon graft 36 is properly positioned in ligament tunnels 32, 34, the bone graft 40 in ligament tunnel 32 of femur 28 is sutured in place with sutures 42. A fixation screw 10 is then inserted into ligament tunnel 32 from anterior surface 29 of femur 28 and tightened. As shown in FIGS. 2 and 4, when fixation screw 10 is inserted into ligament tunnel 32, threaded end 14 of fixation screw 10 is placed between bone graft 40 and bone 44 which surrounds ligament tunnel 32. Handle portion 16 of fixation screw 10 is then twisted to turn fixation screw 10. As fixation screw 10 is turned, threaded end 14 will progressively advance between bone graft 40 and bone 44 and tighten therebetween. As threaded end 14 tightens between bone graft 40 and bone 44, it forces bone graft 40 against bone 44. Threads 15 of threaded end 14 will then begin to deform, since they are made from relatively soft material, as threaded end 14 forces bone graft 40 against bone 44 with ever increasing force. Consequently, threads 15 do not cut into bone graft 40 or bone 44, but deform.

After fixation screw 10 has been tightened in place, threaded end 14 will be disposed between bone graft 40 and bone 44 and forcing bone graft 40 against bone 44 with sufficient force so that bone graft 40 is maintained in place in ligament tunnel 32. As best seen in FIG. 4, threads 15 of threaded end 14 will be deformed or bent over after fixation screw 10 has been tightened. The deformation of threads 15 helps maintain bone graft 40 in place. If bone graft 40 begins to move, some of deformed threads 15 will have originally deformed in a direction to cause them to act against the movement of bone graft 40.

After fixation screw 10 has been tightened, the excess extending beyond the opening of ligament tunnel 32 at anterior surface 29 of femur 28 is trimmed off. This excess portion of fixation screw 10 can be cut off with an osteotome, chizel-like instrument, or the like. The trimmed end of fixation screw 10 will thus be flush with the anterior surface 29 of the femur at the opening of ligament tunnel 32 as shown in FIG. 4. Since the excess of fixation screw 10 can be trimmed after it has been tightened, only one length of fixation screw 10 is required.

Tendon graft 36 is now appropriately tensioned and the bone graft 40 in ligament tunnel 34 in tibia 30 is sutured in place. Another fixation screw 10 is then used to secure bone graft 40 in place in ligament tunnel 34 in similar fashion to that described above. The excess of fixation screw 10 extending beyond anterior surface 31 of tibia 30 at the opening of ligament tunnel 34 is then trimmed off. The trimmed end of fixation screw 10 holding the bone graft 40 in place in ligament tunnel 34 will thus be flush with anterior surface 31 of tibia 30 at the opening of ligament tunnel 34.

In addition to securing tendon grafts in ligament tunnels in knees as just described, interference screw 10 can also be used to secure bone grafts, ligament grafts, or tendon grafts in boney tunnels. Although interference screw 10 has particular use in securing such grafts in boney tunnels in joints of humans, it can also be used to secure such grafts in boney tunnels in joints of animals or in any boney tunnel in an animal.

Although the invention has been described in detail with reference to certain preferred embodiments, materials and specific examples, variations and modifications exist within the scope and spirit of the invention as described and as defined in the following claims.

What is claimed is:

1. A fixation screw for securing a bone graft of a ligament replacement graft in place in a ligament tunnel in a bone by tightening between the bone graft and the bone surrounding the ligament tunnel to force the bone graft against the bone surrounding the ligament tunnel, comprising a body having a threaded end formed as an interference screw from material which is soft compared to bone so that threads of the threaded end do not cut into the bone graft and bone surrounding the ligament tunnel when the fixation screw is tightened, the fixation screw further including integral instrumentation means fabricated as one piece with the threaded end of the body, and of the same material formed as an integral part of the fixation screw for tightening the fixation screw without the need for use of instrumentation separate from the fixation screw, the body having a portion extended outwardly from an entrance to the ligament tunnel after fixation screw is tightened in place wherein said outwardly extending portion can be trimmed off.

2. The fixation screw of claim 1 wherein said material is selected from a biocompatible and a bioabsorbable material.

3. The fixation screw of claim 2 wherein said material is ultra-high molecular weight polyethylene.

4. The fixation screw of claim 1 wherein the integral instrumentation comprises the body having a handle portion connected to the threaded end, the body including the handle portion and threaded end fabricated as one piece.

5. The fixation screw of claim 4 wherein said material is ultra high molecular weight polyethylene.

6. A fixation screw for securing in place in a ligament tunnel extending through a bone in a joint a bone graft of a tendon graft, the tendon graft being used to replace a ligament, the fixation screw comprising a body having a threaded end with threads, the threaded end formed as an interference screw wherein when the fixation screw is tightened is threaded end is tightened between the bone graft and the bone surrounding the bone graft to force the bone graft against the bone to secure the bone graft in place in the ligament tunnel, the fixation screw formed from a material which is soft compared to the bone graft so that the threads of the threaded end do not cut into the bone graft when the fixation screw is tightened, the fixation screw further including integral instrumentation means formed as an integral part of the fixation screw for tightening the fixation screw without the need for use of instrumentation separate from the fixation screw, comprising the body having a handle portion connected to the threaded end, the body including the handle portion and threaded end fabricated as one piece wherein a portion of the body which extends beyond a surface of the bone where the ligament tunnel opens can be trimmed off after the fixation screw is tightened.

7. The fixation screw of claim 6 wherein said material is selected from a biocompatible and a bioabsorbable material.

8. The fixation screw of claim 7 wherein said material is ultra high molecular weight polyethylene.

9. The fixation screw of claim 6 wherein said material is selected from bioabsorbable and biocompatible material.

10. The fixation screw of claim 9 wherein said material is ultra high molecular weight polyethylene or bioabsorbable material.

* * * * *